US011596353B2

United States Patent
Weber et al.

(10) Patent No.: US 11,596,353 B2
(45) Date of Patent: Mar. 7, 2023

(54) MULTILAYER WEARABLE DEVICE

(71) Applicant: Boston Scientific Scimed Inc., Maple Grove, MN (US)

(72) Inventors: Jan Weber, Maastricht (NL); Jeffrey E. Stahmann, Ramsey, MN (US); James M. Peck, Maple Grove, MN (US); Keith R. Maile, New Brighton, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 695 days.

(21) Appl. No.: 16/655,537

(22) Filed: Oct. 17, 2019

(65) Prior Publication Data

US 2020/0121251 A1  Apr. 23, 2020

Related U.S. Application Data

(60) Provisional application No. 62/747,534, filed on Oct. 18, 2018.

(51) Int. Cl.
*A61B 5/00* (2006.01)
*A61B 5/024* (2006.01)
(Continued)

(52) U.S. Cl.
CPC ........ *A61B 5/6831* (2013.01); *A61B 5/02438* (2013.01); *A61B 5/263* (2021.01);
(Continued)

(58) Field of Classification Search
CPC ... A61B 5/6831; A61B 5/263; A61B 5/02438; A61B 5/6832; A61B 5/6833;
(Continued)

(56) References Cited

U.S. PATENT DOCUMENTS

| 6,978,182 B2 | 12/2005 | Mazar et al. | |
| 2009/0076363 A1* | 3/2009 | Bly | A61B 5/02055 600/372 |
| 2016/0171363 A1* | 6/2016 | Mei | A61B 5/6814 235/492 |

OTHER PUBLICATIONS

Liu, Li, et al. (2018). Silicone-based adhesives for long-term skin application: cleaning protocols and their effect on peel strength. Biomedical Physics & Engineering Express, 4:1-11.

* cited by examiner

*Primary Examiner* — Tammie K Marlen
(74) *Attorney, Agent, or Firm* — Faegre Drinker Biddle & Reath LLP

(57) ABSTRACT

Embodiments of the present disclosure relate to monitoring one or more physiological parameters of a subject using a multilayer wearable device. In an embodiment, a multilayer wearable device is configured to be attached to a subject. The multilayer wearable device comprises a substrate having multiple layers including a first portion connected to a second portion. The first portion has a first side and a second, opposite side. And the second portion has a first side and a second, opposite side. The first side of the first portion is configured to be attached to the subject and the second portion is arranged on top of the first portion such that the first side of the second portion is disposed adjacent the second side of the first portion. And, the wearable device includes one or more electrical components configured to sense a physiological parameter of the subject.

16 Claims, 4 Drawing Sheets

(51) Int. Cl.
- *A61L 31/16* (2006.01)
- *A61M 5/00* (2006.01)
- *A61B 5/263* (2021.01)
- *A61M 37/00* (2006.01)

(52) U.S. Cl.
CPC ............ *A61B 5/6832* (2013.01); *A61L 31/16* (2013.01); *A61M 5/00* (2013.01); *A61B 2560/0412* (2013.01); *A61B 2562/164* (2013.01); *A61M 2037/0007* (2013.01)

(58) Field of Classification Search
CPC ......... A61B 5/265; A61B 5/266; A61B 5/268; A61B 5/27; A61B 5/259; A61B 2560/0412; A61B 2562/164; A61M 5/00; A61M 2037/0007; A61N 1/0492; A61N 1/0496; A61L 31/16
See application file for complete search history.

MULTILAYER WEARABLE DEVICE

CROSS-REFERENCE TO RELATED APPLICATION

This application claims priority to Provisional Application No. 62/747,534, filed Oct. 18, 2018, which is herein incorporated by reference in its entirety.

TECHNICAL FIELD

The present disclosure relates to devices and methods for monitoring one or more physiological parameters of a subject. More specifically, the disclosure relates to devices, systems, and methods for monitoring one or more physiological parameters of a subject using a multilayer wearable device.

BACKGROUND

Wearable physiological monitoring systems may provide certain benefits over other non-wearable devices. For example, wearable systems may include a number of sensors that can provide more accurate sensing and data due to their contact with a subject and/or location on a subject.

SUMMARY

Embodiments of the present disclosure relate to monitoring one or more physiological parameters of a subject using a multilayer wearable device. Examples of wearable devices include but are not limited to the following.

In an Example 1, a multilayer wearable device is configured to be attached to a subject, the multilayer wearable device comprises: a substrate having multiple layers, the substrate comprising a first portion connected to a second portion, the first portion having a first side and a second, opposite side, and the second portion having a first side and a second, opposite side; wherein the first side of the first portion is configured to be attached to the subject and the second portion is arranged on top of the first portion such that the first side of the second portion is disposed adjacent the second side of the first portion; and one or more electrical components arranged on the substrate, wherein at least one of the one or more electrical components is configured to sense a physiological parameter of the subject.

In an Example 2, the multilayer wearable device of Example 1, wherein the second portion has a greater thickness than the first portion.

In an Example 3, the multilayer wearable device of any one of Examples 1-2, wherein the first portion is flexible and stretchable.

In an Example 4, the multilayer wearable device of any one of Examples 1-3, wherein the first portion is porous to an active pharmaceutical ingredient such that the active pharmaceutical ingredient is able to transmit through the first portion to the subject.

In an Example 5, the multilayer wearable device of Example 4, further comprising a first electrode arranged on the second side of the first portion and a second electrode arranged on the first side of the second portion, wherein the first electrode is not electrically connected to the second electrode, wherein the first electrode and the second electrode facilitate delivery of the active pharmaceutical ingredient to the subject.

In an Example 6, the multilayer wearable device of any one of Examples 1-5, further comprising a gel layer arranged between the first portion and the second portion.

In an Example 7, the multilayer wearable device of Example 6, the gel layer further comprising particles configured to facilitate separation between the first portion and the second portion.

In an Example 8, the multilayer wearable device of any one of Examples 1-7, the one or more electrical components comprising a capacitor arranged between the first portion and the second portion, wherein the capacitor facilitates measuring a pressure applied to the multilayer wearable device.

In an Example 9, the multilayer wearable device of any one of Examples 1-8, wherein the thickness of the substrate is less than or equal to approximately 10 micrometers.

In an Example 10, the multilayer wearable device of any one of Examples 1-9, the substrate comprising a third portion connected to the second portion, the third portion having a first side and a second, opposite side, wherein the third portion is arranged on top of the second portion such that the first side of the third portion is disposed adjacent the second side of the second portion.

In an Example 11, the multilayer wearable device of any one of Examples 1-10, wherein a width of an outer envelope of the first portion is greater than or equal to a width of an outer envelope of the second portion.

In an Example 12, a method of manufacturing a multilayer wearable device configured to be attached to a subject, the method comprises: arranging one or more electronic components on a substrate, wherein at least one of the one or more electrical components is configured to sense a physiological parameter of the subject; and arranging the substrate to form a multilayer wearable device, wherein a first junction separates a first portion and a second portion, the first portion connected to the second portion, the first portion having a first side and a second, opposite side, and the second portion having a first side, and a second, opposite side; and wherein the first side of the first portion is configured to be attached to the subject, and the second portion is arranged on top of the first portion such that the first side of the second portion is disposed adjacent the second side of the first portion.

In an Example 13, the method of Example 12, further comprising disposing a gel on the second side of the first portion.

In an Example 14, the method of any one of Examples 12-13, the method further comprising disposing a first electrode on the second side of the first portion and a second electrode on the first side of the second portion, wherein the first electrode is not electrically connected to the second electrode, wherein the first electrode and the second electrode facilitate delivery of an active pharmaceutical ingredient to the subject.

In an Example 15, the method of any one of Examples 12-14, further comprising arranging the substrate so that a second junction separates the second portion and a third portion, the third portion having a first side and a second, opposite side, wherein the third portion is arranged on top of the second portion such that the first side of the third portion is disposed adjacent the second side of the second portion.

In an Example 16, a multilayer wearable device is configured to be attached to a subject, the multilayer wearable device comprises: a substrate having multiple layers, the substrate comprising a first portion connected to a second portion, the first portion having a first side and a second, opposite side, and the second portion having a first side and a second, opposite side; wherein the first side of the first portion is configured to be attached to the subject and the second portion is arranged on top of the first portion such that the first side of the second portion is disposed adjacent the second side of the first portion; and one or more electrical components arranged on the substrate, wherein at least one of the one or more electrical components is configured to sense a physiological parameter of the subject.

In an Example 17, the multilayer wearable device of Example 16, wherein the second portion has a greater thickness than the first portion.

In an Example 18, the multilayer wearable device of Example 16, wherein the first portion is flexible and stretchable.

In an Example 19, the multilayer wearable device of Example 16, wherein the first portion is porous to an active pharmaceutical ingredient such that the active pharmaceutical ingredient is able to transmit through the first portion to the subject.

In an Example 20, the multilayer wearable device of Example 19, further comprising a first electrode arranged on the second side of the first portion and a second electrode arranged on the first side of the second portion, wherein the first electrode is not electrically connected to the second electrode, wherein the first electrode and the second electrode facilitate delivery of the active pharmaceutical ingredient to the subject.

In an Example 21, the multilayer wearable device of Example 16, further comprising a gel layer arranged between the first portion and the second portion.

In an Example 22, the multilayer wearable device of Example 21, the gel layer further comprising particles configured to facilitate separation between the first portion and the second portion.

In an Example 23, the multilayer wearable device of Example 16, the one or more electrical components comprising a capacitor arranged between the first portion and the second portion, wherein the capacitor facilitates measuring a pressure applied to the multilayer wearable device.

In an Example 24, the multilayer wearable device of Example 16, wherein the thickness of the substrate is less than or equal to approximately 10 micrometers.

In an Example 25, the multilayer wearable device of Example 16, the substrate comprising a third portion connected to the second portion, the third portion having a first side and a second, opposite side, wherein the third portion is arranged on top of the second portion such that the first side of the third portion is disposed adjacent the second side of the second portion.

In an Example 26, the multilayer wearable device of Example 16, wherein a width of an outer envelope of the first portion is greater than or equal to a width of an outer envelope of the second portion.

In an Example 27, a method of manufacturing a multilayer wearable device configured to be attached to a subject, the method comprises: arranging one or more electronic components on a substrate, wherein at least one of the one or more electrical components is configured to sense a physiological parameter of the subject; and arranging the substrate to form a multilayer wearable device, wherein the first junction separates a first portion and a second portion, the first portion connected to the second portion, the first portion having a first side and a second, opposite side, and the second portion having a first side, and a second, opposite side; and wherein the first side of the first portion is configured to be attached to the subject, and the second portion is arranged on top of the first portion such that the first side of the second portion is disposed adjacent the second side of the first portion.

In an Example 28, the method of Example 27, further comprising disposing a gel on the second side of the first portion.

In an Example 29, the method of Example 28, the gel layer further comprising particles configured to facilitate separation between the first portion and the second portion.

In an Example 30, the method of Example 27, the method further comprising disposing a first electrode on the second side of the first portion and a second electrode on the first side of the second portion, wherein the first electrode is not electrically connected to the second electrode, wherein the first electrode and the second electrode facilitate delivery of an active pharmaceutical ingredient to the subject.

In an Example 31, the method of Example 27, further comprising arranging the substrate so that a second junction separates the second portion and a third portion, the third portion having a first side and a second, opposite side, wherein the third portion is arranged on top of the second portion such that the first side of the third portion is disposed adjacent the second side of the second portion.

In an Example 32, the method of Example 31, further comprising disposing a gel on the second side of the second portion.

In an Example 33, the method of Example 27, wherein the second portion has a greater thickness than the first portion.

In an Example 34, the method of Example 28, further comprising forming pores in the first portion, wherein the pores are porous to an active pharmaceutical ingredient such that the active pharmaceutical ingredient is able to transmit through the first portion to the subject.

In an Example 35, the method of Example 27, wherein the second portion has a greater thickness than the first portion.

While multiple embodiments are disclosed, still other embodiments of the present disclosure will become apparent to those skilled in the art from the following detailed description, which shows and describes illustrative embodiments of the disclosure. Accordingly, the drawings and detailed description are to be regarded as illustrative in nature and not restrictive.

Figure 1:
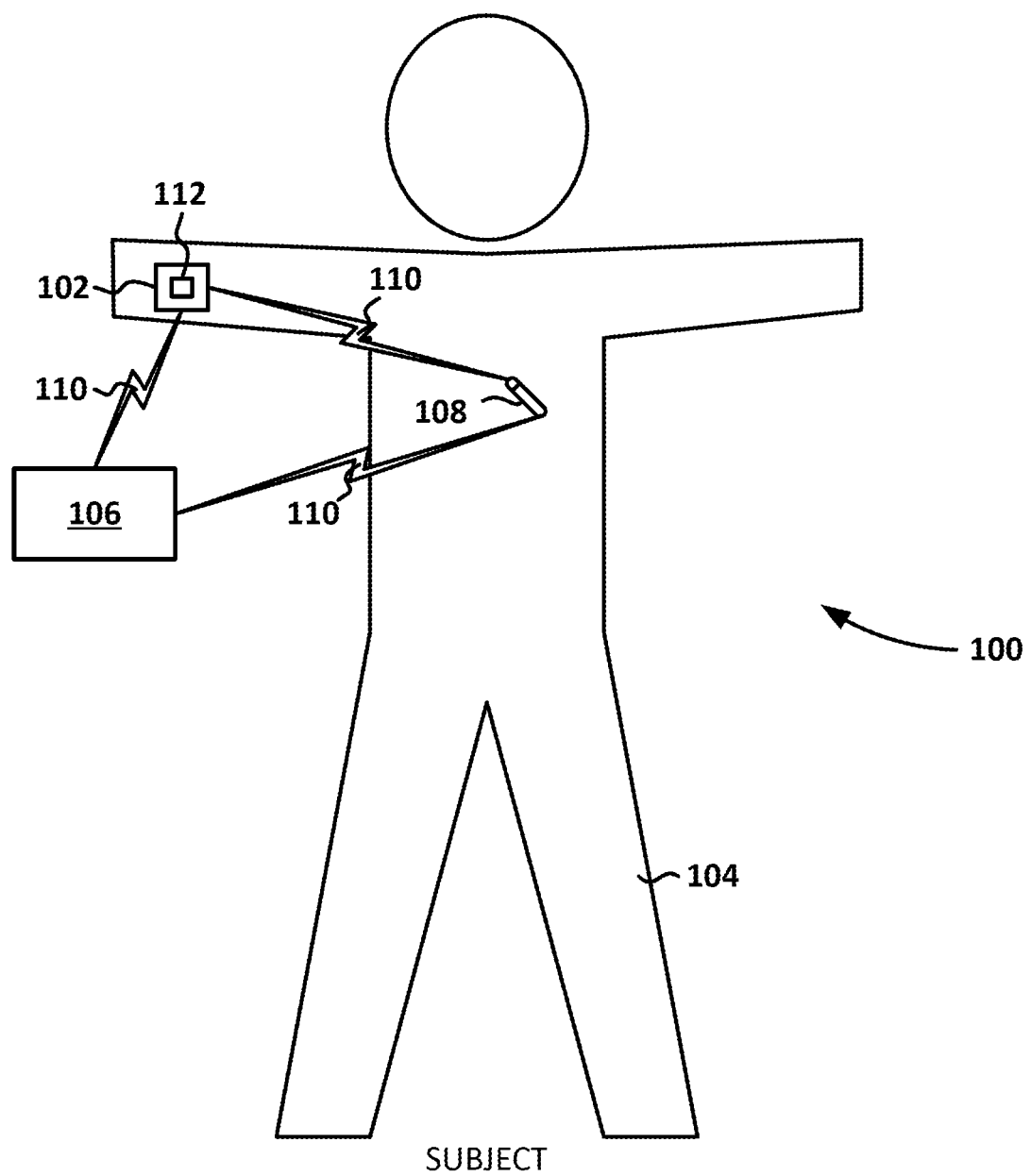
FIG. 1 is a schematic illustration of a medical system including a multilayer wearable device, in accordance with embodiments of the disclosure.

While the disclosed subject matter is amenable to various modifications and alternative forms, specific embodiments have been shown by way of example in the drawings and are described in detail below. The intention, however, is not to limit the subject matter disclosed herein to the particular embodiments described. On the contrary, the disclosure is intended to cover all modifications, equivalents, and alternatives falling within the scope of the subject matter disclosed herein, and as defined by the appended claims.

As used herein in association with values (e.g., terms of magnitude, measurement, and/or other degrees of qualitative and/or quantitative observations that are used herein with respect to characteristics (e.g., dimensions, measurements, attributes, components, etc.) and/or ranges thereof, of tangible things (e.g., products, inventory, etc.) and/or intangible things (e.g., data, electronic representations of currency, accounts, information, portions of things (e.g., percentages, fractions), calculations, data models, dynamic system models, algorithms, parameters, etc.), "about" and "approximately" may be used, interchangeably, to refer to a value, configuration, orientation, and/or other characteristic that is equal to (or the same as) the stated value, configuration, orientation, and/or other characteristic or equal to (or the same as) a value, configuration, orientation, and/or other characteristic that is reasonably close to the stated value, configuration, orientation, and/or other characteristic, but that may differ by a reasonably small amount such as will be understood, and readily ascertained, by individuals having ordinary skill in the relevant arts to be attributable to measurement error; differences in measurement and/or manufacturing equipment calibration; human error in reading and/or setting measurements; adjustments made to optimize performance and/or structural parameters in view of other measurements (e.g., measurements associated with other things); particular implementation scenarios; imprecise adjustment and/or manipulation of things, settings, and/or measurements by a person, a computing device, and/or a machine; system tolerances; control loops; machine-learning; foreseeable variations (e.g., statistically insignificant variations, chaotic variations, system and/or model instabilities, etc.); preferences; and/or the like.

The terms "up," "upper," and "upward," and variations thereof, are used throughout this disclosure for the sole purpose of clarity of description and are only intended to refer to a relative direction (i.e., a certain direction that is to be distinguished from another direction) and are not meant to be interpreted to mean an absolute direction. Similarly, the terms "down," "lower," and "downward," and variations thereof, are used throughout this disclosure for the sole purpose of clarity of description and are only intended to refer to a relative direction that is at least approximately opposite a direction referred to by one or more of the terms "up," "upper," and "upward," and variations thereof.

Although the term "block" may be used herein to connote different elements illustratively employed, the term should not be interpreted as implying any requirement of, or particular order among or between, various blocks disclosed herein. Similarly, although illustrative methods may be represented by one or more drawings (e.g., flow diagrams, communication flows, etc.), the drawings should not be interpreted as implying any requirement of, or particular order among or between, various steps disclosed herein. However, certain embodiments may require certain steps and/or certain orders between certain steps, as may be explicitly described herein and/or as may be understood from the nature of the steps themselves (e.g., the performance of some steps may depend on the outcome of a previous step). Additionally, a "set," "subset," or "group" of items (e.g., inputs, algorithms, data values, etc.) may include one or more items, and, similarly, a subset or subgroup of items may include one or more items. A "plurality" means more than one.

DETAILED DESCRIPTION

For a wearable device to be directly connected to a subject and stay attached for a number of days or even weeks, the wearable device may be thin, flexible and stretchable. For that reason, thin substrates (e.g., below 10 micrometer), meandering conductive traces, and thinned-down silicon chips may be utilized. A potential drawback of such a construction is that the wearable device may become fragile, difficult to handle and construct. On the other, complex circuits, including sensors, communication elements, processors and power sources, may require a robust platform such as a "thick" substrate with plenty of surface area.

Embodiments disclosed herein address these problems, and others, by disclosing a multilayer wearable device. In embodiments, the multilayer wearable device may be flexible and/or stretchable. The flexible and/or stretchable characteristics of the multilayer wearable device may allow the multilayer wearable device to be placed in positions on a subject where another, more rigid device may not be able to be placed and/or where a more rigid device may be uncomfortable for the subject. As such, the multilayer wearable device may be able to sense parameters that a more rigid device may not be able to sense. Additionally or alternatively, due to the multiple layers of the multilayer wearable device, more electronic components may be arranged on the multilayer wearable device while maintaining a smaller contact interface between the multilayer wearable device and a subject than if the wearable device were a single layer. As such, the multilayer wearable device may have the same or a smaller footprint than another single-layer wearable device while providing more functionality and more robustness than the single-layer wearable device. These are only examples of some of the advantages of the embodiments disclosed herein, though, and should not be considered limiting.

FIG. 1 is a schematic illustration of a system 100 including a multilayer wearable device 102 arranged on a subject 104, in accordance with embodiments of the disclosure. The multilayer wearable device 102 may be positioned adjacent the body of a subject 104 and/or disposed on the body of the subject 104. The subject 104 may be a human, a dog, a pig, and/or any other animal having physiological parameters that can be recorded. For example, in embodiments, the subject 104 may be a human patient.

In addition to the multilayer wearable device 102, the system 100 may include one or more other devices 106, 108. In embodiments, the device 106 may be configured to be positioned adjacent the body of a subject 104, disposed on the body of the subject 104, and/or spaced apart from the subject 104. In embodiments, the device 108 may be implanted within the body of a subject 104.

In embodiments, the multilayer wearable device 102 and one or more of the devices 106, 108 may be communicatively coupled via a communication link 110. In embodiments, the communication link 110 may be, or include, a wired link (e.g., a link accomplished via a physical connection) and/or a non-wired communication link such as, for example, a short-range radio link, such as Bluetooth, Bluetooth Low Energy, IEEE 802.11, near-field communication (NFC), WiFi, a proprietary wireless protocol, optical, and/or the like. The term "communication link" may refer to an ability to communicate some type of information in at least one direction between at least two devices, and should not be understood to be limited to a direct, persistent, or otherwise limited communication channel. That is, according to embodiments, the communication link 110 may be a persistent communication link, an intermittent communication link, an ad-hoc communication link, and/or the like. The communication link 110 may refer to direct communications between the multilayer wearable device 102 and one or more of the devices 106, 108, and/or indirect communications that travel between the multilayer wearable device 102 and one or more of the devices 106, 108 via at least one other device (e.g., a repeater, router, hub, and/or the like). The communication link 110 may facilitate uni-directional and/or bi-directional communication between multilayer wearable device 102 and one or more of the devices 106, 108. Data and/or control signals may be transmitted between the multilayer wearable device 102 and one or more of the devices 106, 108. In embodiments, subject data may be downloaded from one or more of the multilayer wearable device 102 and the devices 106, 108 periodically or on command. The clinician, an at-home care provider, and/or the subject 104 may communicate with the multilayer wearable device 102 and one or more of the devices 106, 108, for example, to acquire subject data or to initiate, terminate and/or modify recording and/or therapy. In embodiments, the communication link 110 may facilitate encryption and/or other methods to increase data transmission safety.

In embodiments, the multilayer wearable device 102 and/or one or more of the devices 106, 108 may provide one or more of the following functions with respect to a subject: sensing, data storage, data analysis, presentation, and/or therapy. For example, in embodiments, the multilayer wearable device 102 and/or one or more of the devices 106, 108 may be used to measure any number of a variety of physiological, device, subjective, and/or environmental parameters associated with the subject 104, using electrical, mechanical, optical, and/or chemical means. The multilayer wearable device 102 and/or one or more of the devices 106, 108 may be configured to automatically gather data, gather data upon request (e.g., input provided by the subject, a clinician, another device, and/or the like), gather data in response to an event, and/or any number of various combinations and/or modifications thereof. The multilayer wearable device 102 and/or one or more of the devices 106, 108 may be configured to store data related to the physiological, device, environmental, and/or subjective parameters and/or transmit the data to any number of other devices in the system 100. The environmental parameters may include particulates, temperature, ultraviolet light, volatile organic compounds, temperature, altitude, location, ambient light, humidity, sound, electromagnetic radiation, barometric pressure, and/or the like in the environment. The physiological parameters may include respiratory parameters (e.g., rate, depth, rhythm), motion parameters (e.g., walking, running, falling, gait, gait rhythm), micro-motion parameters (e.g., trembling), facial expressions, swelling, heart sounds, sweat, fluids (e.g. sweat, blood, urine, tears, saliva, intercellular fluid, cerebrospinal fluid, fluid composition (e.g., ammonia, pH, potassium, sodium, chloride)), exhaled air composition, Electrocardiography (ECG) parameters, electroencephalogram (EEG) parameters, Electromyography (EMG) parameters, and/or the like. In embodiments, the multilayer wearable device 102 may include processing devices configured to process the sensed parameters, memory to store the sensed parameters, transmitters to transmit the sensed parameters, and/or receivers to receive one or more transmissions.

In embodiments, the multilayer wearable device 102 and/or one or more of the devices 106, 108 may be configured to analyze data and/or act upon the analyzed data. For example, the multilayer wearable device 102 and/or one or more of the devices 106, 108 may be configured to modify therapy, perform additional monitoring, store pre-analyzed or post-analyzed data, and/or provide alarm indications based on the analysis of the data.

In embodiments, the multilayer wearable device 102 and/or one or more of the devices 106, 108 may be configured to provide therapy. Therapy may be provided autonomously and/or upon request (e.g., an input by the subject 104, a clinician, another device or process, and/or the like). The multilayer wearable device 102 and/or one or more of the devices 106, 108 may be programmable in that various characteristics of their sensing, therapy (e.g., duration and interval), and/or communication may be altered by communication between the multilayer wearable device 102 and the one or more of the devices 106, 108. For example, in embodiments, one or more of the devices 106, 108 may be configured to communicate with the multilayer wearable device 102 to trigger the multilayer wearable device 102 to perform an action (e.g., a sensing action, a therapy action, etc.). In this manner, for example, timing of various activities performed by the multilayer wearable device 102 may be configured and maintained based on a communication scheme involving a number of the devices of the system 100.

According to embodiments, the multilayer wearable device 102 may include any number of different types of devices configured to be placed on, coupled to, embedded in, and/or otherwise interfaced with a subject's body (e.g., skin). In embodiments, the multilayer wearable device 102 is a multilayer, relatively low profile device resembling a tattoo or sticker. The multilayer wearable device 102 may be configured to include circuitry that facilitates sensing and/or therapy functions. In embodiments, the multilayer wearable device 102 may include an adhesive layer that facilitates the multilayer wearable device 102 being attached to the subject 104. Additionally or alternatively, the multilayer wearable device 102 may be attached to the subject 104 using another adhesive and/or compound not included in the multilayer wearable device 102. Additionally or alternatively, the multilayer wearable device 102 may be stamped and/or printed on the subject 104.

In embodiments, at least the first layer (the layer that is in contact with the subject) of the multilayer wearable device 102 may be deformable so that the multilayer wearable device 102 is able to form to different contours of a subject 104 and/or flex and/or stretch, thereby accommodating movement of the subject 104. Due to the multilayer wearable device 102 deformation ability, the multilayer wearable device 102 may be able to be placed on different areas of the subject 104. For example, the multilayer wearable device 102 may be placed on one or more of the following areas of the subject 104: abdomen, chest, back, wrist, thigh, calve, foot, ankles, arm, hands, eyelids, ears, earlobes, penis, forehead, neck, and/or the like. These placements may facilitate sensing one or more environmental and/or physiological parameters set forth above.

Additionally or alternatively, the multilayer wearable device 102 may allow gases and/or liquids to permeate all or certain portions of the multilayer wearable device 102. The gas and/or liquid flow may be bidirectional or unidirectional. The multilayer wearable device 102 may allow some gases and/or liquids to permeate the multilayer wearable device 102 while preventing flow of other gases and/or liquids.

While one multilayer wearable device 102 is depicted in FIG. 1, in embodiments, there may be multiple multilayer wearable devices 102 positioned adjacent the body of a subject 104 and/or disposed on the body of the subject 104. In embodiments, each multilayer wearable device 102 may be configured to perform the same function as the other multilayer wearable devices 102 or perform different functions from the same or different locations. For example, a multilayer wearable device 102 may be placed on the chest of the subject 104 to record thoracic sounds and a multilayer wearable device 102 may be placed on the eyelid of the subject 104 to record eye movements (e.g., eyelid movements) indicative of REM sleep. Additionally or alternatively, a series of multilayer wearable devices 102 may be placed (e.g., subsequently in time) on a subject 104 whereby information from a first multilayer wearable device 102 may be used to adjust and/or modify functionality of an additional multilayer wearable device 102 such as, for example, an additional tattoo that was placed on the subject 104 at a later time than that of the first multilayer wearable device 102, that is configured to perform an action at a later time than the first multilayer wearable device 102, and/or the like.

According to embodiments, a number of multilayer wearable devices 102 may be configured to perform one or more functions in a cooperative manner, the cooperation of which may be managed by one or more of the multilayer wearable devices 102, the device 106 and/or the device 108. That is, for example, one or more multilayer wearable devices may be configured to transmit a signal (e.g., an acoustic signal, an electric signal, an optical signal, etc.), and one or more other multilayer wearable devices 102 may be configured to receive the transmitted signal and evaluate the attenuation or other characteristic of the signal to determine a characteristic about the media through which the signal traveled (e.g., to identify edema, measure transthoracic impedance, perform pulse oximetry, etc.). In embodiments, one or more multilayer wearable devices may be configured to cooperatively sense physiological parameters, provide coordinated therapy, and/or the like.

According to embodiments, the device 106 may be a wearable device (e.g., smartwatch), a portable computing device (e.g., smartphone), a medical device (e.g., a wearable medical device (WMD)), and/or the like. For example, the device 106 may include a control device, a monitoring device, a respiratory device, a pacemaker, a cardiac resynchronization therapy (CRT) device and/or the like, and may be a wearable device and/or medical device known in the art or later developed, for sensing physiological parameters of the subject 104, providing therapy and/or diagnostic data about the subject 104 and/or the device 106. In various embodiments, the device 106 may include inhaler functionality, nebulizer functionality, ventilating functionality, defibrillation, and pacing/CRT capabilities (e.g., a CRT-D device). In embodiments, the device 106 may be wearable on the subject 104 and may be configured to monitor (e.g., sense and/or record) physiological parameters associated with subject 104 (e.g., respiratory system, and/or circulatory system). In embodiments, the device 106 may be configured to record physiological parameters such as, for example, one or more respiratory signals, cardiac electrical signals, spirometry, oximetry, arterial blood gas measurements, heart sounds, heart rate, blood pressure measurements, oxygen saturations, and/or the like.

Additionally or alternatively, the device 106 may or may not be positioned adjacent the body of a subject 104 and/or disposed on the body of the subject 104. In embodiments, the device 106 may store data (e.g., medical data) and/or provide data to the multilayer wearable device 102 and/or the device 108 via a communication link 110. The data provided by the device 106 to one or more of the devices 102, 108 may facilitate one or more of the devices 102, 108 functioning as described above and below.

According to embodiments, the devices 106, 108 may include any type of medical device (e.g., an implantable medical device (IMD), etc.) that senses one or more physiological parameters of the subject 104, administers one or more therapies, and/or the like, and may include any number of different components of a medical device. For example, the device 108 may include a control device, a monitoring device, a respiratory device, a pacemaker, an implantable cardioverter defibrillator (ICD), a cardiac resynchronization therapy (CRT) device, a neurostimulation device, a drug delivery device, a muscular stimulation device, an optimal or audio stimulation device, and/or the like, and may be a medical device known in the art or later developed, for sensing physiological parameters, providing therapy and/or diagnostic data about the subject 104 and/or the device 108. In various embodiments, the device 108 may include a drug delivery functionality (e.g., an inhaler functionality, a nebulizer functionality and/or the like), ventilating functionality, defibrillation, an air filtration functionality, a smoking cessation functionality, an oxygen delivery functionality, a volatile compound release functionality, and/or pacing/CRT capabilities (e.g., a CRT-D device). In embodiments, the device 108 may be implanted subcutaneously within an implantation location or pocket in the patient's chest or abdomen and may be configured to monitor (e.g., sense and/or record) physiological parameters associated with one or more body systems of the subject 104 (e.g., the respiratory system, the nervous system, and/or the circulatory system). In embodiments, the device 108 may be an implantable respiratory monitor, an implantable cardiac monitor (ICM) (e.g., an implantable diagnostic monitor (IDM), an implantable loop recorder (ILR), etc.) configured to record physiological parameters such as, for example, one or more respiratory signals, cardiac electrical signals, spirometry, oximetry, arterial blood gas measurements, heart sounds, heart rate, blood pressure measurements, oxygen saturations, and/or the like.

In addition, the multilayer wearable device 102 may include one or more sensors 112 configured to detect a variety of physiological parameters and/or environmental parameters that may be used in connection with various diagnostic, therapeutic and/or monitoring implementations. For example, the multilayer wearable device 102 may include sensors or circuitry for detecting respiratory system signals, cardiac system signals, heart sounds, and/or signals related to subject's 104 activity. In embodiments, the multilayer wearable device 102 may be configured to sense intrathoracic impedance, from which various respiratory parameters may be derived, including, for example, respiratory tidal volume and minute ventilation. Sensors and associated circuitry may be incorporated in connection with the multilayer wearable device 102 for detecting one or more body movement or body posture and/or position related signals. For example, accelerometers, gyroscopes, and/or GPS devices may be employed to detect patient activity, patient location, body orientation, and/or torso position.

Derived parameters may also be monitored using the multilayer wearable device 102. For example, a respiration sensor may rely on measurements taken by an implanted accelerometer that measures body activity levels, respiration sounds, chest movement with respiration, heart sounds, and/or the like. The respiration sensor may include one or more electrodes configured to sense a physiological electrical signal, from which a respiration signal may be extracted. Respiration signals may additionally, or alternatively, be extracted from heart sound signals, cardiac electrical signals (e.g., electrograms), and/or the like. The respiration sensor may be used to estimate respiration patterns based on the measured parameters.

As stated above, a sensor 112 may be configured to sense physiological information about the subject 104. The physiological information may include at least one of: a respiration sensor, a sound sensor, a heart rate sensor, an oxygen sensor, a muscle use sensor, an activity sensor, a posture sensor, an inflammation sensor, a chemical sensor, an exhaled breath sensor, a thoracic composition sensor, an altered consciousness sensor, a central cyanosis sensor, and a sleep quality sensor. In embodiments, the multilayer wearable device 102 may include sensing components such as, for example, one or more surface electrodes configured to obtain an electrocardiogram (ECG), one or more accelerometers configured to detect motion associated with the subject 104, one or more respiratory sensors configured to obtain respiration information associated with the subject 104, one or more environmental sensors configured to obtain information about the external environment (e.g., temperature, air quality, humidity, carbon monoxide level, oxygen level, barometric pressure, light intensity, sound, and/or the like) to which the subject 104 is exposed, and/or the like. In embodiments, the multilayer wearable device 102 may be configured to measure parameters relating to the human body, such as temperature (e.g., a thermometer), blood pressure (e.g., a sphygmomanometer), blood characteristics (e.g., glucose levels), force (e.g., impact force of feed during walking), body weight, physical strength, mental acuity, heart characteristics, relative geographic position (e.g., a Global Positioning System (GPS)), and/or the like.

Respiration sensors can be used to determine tidal volume (VT), respiration rate, peak expiratory flow rate (PEFR), forced expiratory volume (FEV), and a composite respiration index that includes at least one of an inspiration/expiration ratio (IER), VT times respiration rate, and respiration rate divided by VT. Respiration sensors may include any number of different types of sensors, including thoracic impedance sensors, accelerometers, flow sensors, and electrocardiograms (ECG or EKG). For example, the respiration rate can be sensed by one or more of a thoracic impedance sensor, an accelerometer, and an ECG. Also, the PEFR and the FEV can be determined using a thoracic impedance sensor to measure VT, and the IER can be determined using a thoracic impedance to measure VT. Other parameters associated with a respiratory functional test can also be used in determining asthma status. These parameters include the VT, FEV, and PEFR parameters, minute volume (MV), vital capacity (VC), functional residual capacity (FRC), total lung capacity, forced vital capacity (FVC), and forced expiratory flow (FEF).

Sound sensors can include at least one of a lung sound sensor, a speech sensor, and a heart sound sensor, where the lung sound sensor can be configured to sense wheezing in the patient. In embodiments, sound sensors include one or more of an accelerometer, a hydrophone, and a microphone. For example, a speech sensor and a lung sound sensor for sensing wheezing can include one or more of an accelerometer and a microphone.

In embodiments, a heart rate sensor includes an ECG for measuring the heart rate, an oxygen sensor includes an optical oxygen saturation sensor, and a central cyanosis sensor includes an optical oxygen saturation sensor. Also, in embodiments, a muscle use sensor and an activity sensor include one or more of a cervical and thoracic impedance sensor and an electromyogram for measuring activity. In addition, a posture sensor and an altered consciousness sensor include an accelerometer for measuring posture and/or balance. The inflammation sensor includes a chemical sensor for detecting an inflammatory marker, such as nitric oxide, and the sleep quality sensor includes one or more of a thoracic impedance sensor, an accelerometer, and an ECG for measuring tidal volume, respiration rate activity, posture, and heart rate. In embodiments, a sleep monitoring sensor may include an accelerometer that is incorporated into the e-tattoo 106 that is positioned on the eyelid of the subject 104.

In embodiments, a chemical sensor includes one or more of an inflammatory marker, e.g., a C-reactive protein, a pharmaceutical agent, e.g., theophylline, beta blockers, and/or aspirin, a blood gas, e.g., oxygen and/or carbon dioxide, and blood cell count, e.g., an eosinophil count. In embodiments, for example, a breath sensor includes a chemical sensor such as, for example, a nitric oxide test, where increased levels of exhaled nitric oxide indicate inflammation, which can, for example, indicate a worsening asthma status.

As explained in more detail below in relation to FIG. 3, the multilayer wearable device 102 includes multiple layers that facilitate including more electronic components thereon, providing more functionality, and/or increasing the structural integrity of the multilayer wearable device 102.

The illustrative system 100 shown in FIG. 1 is not intended to suggest any limitation as to the scope of use or functionality of embodiments of the present disclosure. The illustrative system 100 should not be interpreted as having any dependency or requirement related to any single component or combination of components illustrated therein. Additionally, various components depicted in FIG. 1 may be, in embodiments, integrated with various ones of the other components depicted therein (and/or components not illustrated), all of which are within the ambit of the subject matter disclosed herein.

Various components depicted in FIG. 1 may operate together to form the system 100, which may be, for example, a computerized patient management and monitoring system. In embodiments, the system 100 may be designed to assist in monitoring the subject's condition, managing the subject's therapy, and/or the like. An illustrative patient management and monitoring system is the LATITUDE® patient management system from Boston Scientific Corporation, Marlborough, Mass. Illustrative aspects of a patient management and monitoring system are described in ADVANCED PATIENT MANAGEMENT SYSTEM INCLUDING INTERROGATOR/TRANSCEIVER UNIT, U.S. Pat. No. 6,978,182 to Mazar et al., the entirety of which is hereby incorporated by reference herein.

Various components depicted in FIG. 1 may operate together to form the system 100, which may be, for example, a computerized patient management and monitoring system. In embodiments, the system 100 may be designed to assist in monitoring the subject's condition, managing the subject's therapy, and/or the like. An illustrative patient management and monitoring system is the LATITUDE® patient management system from Boston Scientific Corporation, Marlborough, Mass. Illustrative aspects of a patient management and monitoring system are described in ADVANCED PATIENT MANAGEMENT SYSTEM INCLUDING INTERROGATOR/TRANSCEIVER UNIT, U.S. Pat. No. 6,978,182 to Mazar et al., the entirety of which is hereby incorporated by reference herein.

Figure 2:
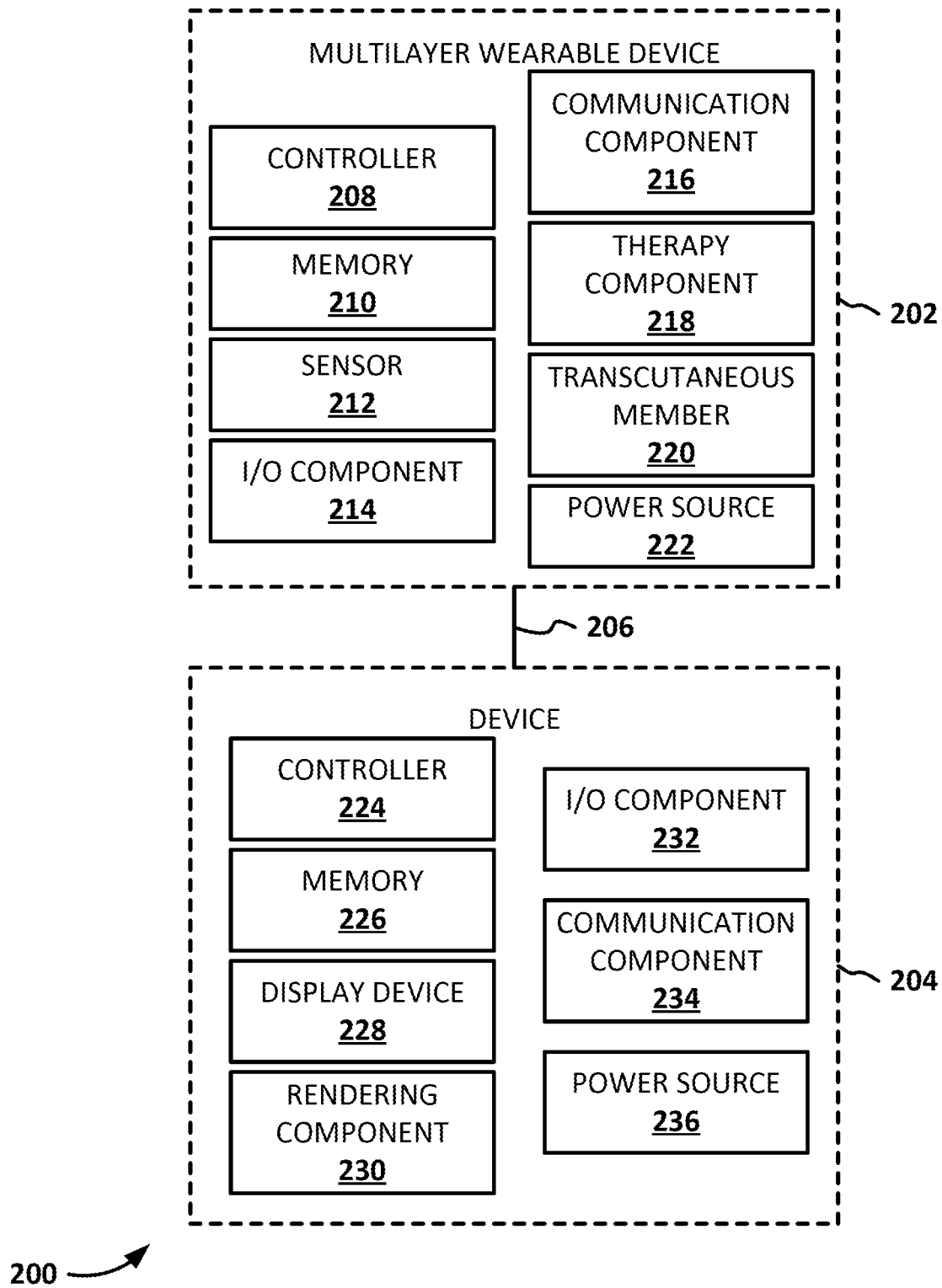
FIG. 2 is a block diagram depicting an illustrative operating environment, in accordance with embodiments of the subject matter disclosed herein.

FIG. 2 is a block diagram depicting an illustrative operating environment 200, in accordance with embodiments of the subject matter disclosed herein. According to embodiments, the operating environment 200 may be, be similar to, include, be included in, or correspond to the system 100 depicted in FIG. 1. As shown in FIG. 2, the illustrative operating environment 200 includes a multilayer wearable device 202 configured to communicate with a device 204 via a communication link 206. In embodiments, the operating environment 200 may include the multilayer wearable device 202 without including the device 204.

According to embodiments, the multilayer wearable device 202 may be, be similar to, include, or be included in the multilayer wearable device 102 depicted in FIG. 1. The device 204 may be, be similar to, include, or be included in the device 106 and/or the device 108 depicted in FIG. 1. And, similarly, the communication link 206 may be, be similar to, include, or be included in the communication link 110 depicted in FIG. 1. According to embodiments, the operating environment 200 may include any number of other devices and/or any other types of devices, for example, additional medical devices, mobile devices, additional multilayer wearable devices, and/or the like.

According to embodiments illustrated in FIG. 2, the multilayer wearable device 202 includes a controller 208, a memory 210, a sensor 212, an input/output (I/O) component 214, a communication component 216, a therapy component 218, a transcutaneous member 220, and/or a power source 222.

The controller 208 may include, for example, a processing unit, a pulse generator, and/or the like. The controller 208 may be any arrangement of electronic circuits, electronic components, processors, program components and/or the like configured to store and/or execute programming instructions, to direct the operation of the other functional components of the multilayer wearable device 202, to instruct the sensor 212 to sense one or more physiological parameters of a subject (e.g., the subject 104), to instruct the sensor 212 to sense one or more environmental parameters, to store physiologic data obtained by the sensor 212, to instruct the therapy component 218 to provide one or more therapies, and/or the like, and may be implemented, for example, in the form of any combination of hardware, software, and/or firmware.

In embodiments, the controller 208 may be, include, or be included in one or more Field Programmable Gate Arrays (FPGAs), one or more Programmable Logic Devices (PLDs), one or more Complex PLDs (CPLDs), one or more custom Application Specific Integrated Circuits (ASICs), one or more dedicated processors (e.g., microprocessors), one or more central processing units (CPUs), software, hardware, firmware, or any combination of these and/or other components. According to embodiments, the controller 208 may include a processing unit configured to communicate with memory to execute computer-executable instructions stored in the memory. Although the controller 208 is referred to herein in the singular, the controller 208 may be implemented in multiple instances, distributed across multiple computing devices, instantiated within multiple virtual machines, and/or the like.

The controller 208 may also be configured to store information in the memory 210 and/or access information from the memory 210. The controller 208 may execute instructions and perform desired tasks as specified by computer-executable instructions stored in the memory 210.

In embodiments, the memory 210 includes computer-readable media in the form of volatile and/or nonvolatile memory and may be removable, nonremovable, or a combination thereof. Media examples include Random Access Memory (RAM); Read Only Memory (ROM); Electronically Erasable Programmable Read Only Memory (EEPROM); flash memory; optical or holographic media; magnetic cassettes, magnetic tape, magnetic disk storage or other magnetic storage devices; data transmissions; and/or any other medium that can be used to store information and can be accessed by a computing device such as, for example, quantum state memory, and/or the like. In embodiments, the memory stores computer-executable instructions for causing the processor to implement aspects of embodiments of system components discussed herein and/or to perform aspects of embodiments of methods and procedures discussed herein.

The computer-executable instructions may include, for example, computer code, machine-useable instructions, and the like such as, for example, program components capable of being executed by one or more processors associated with the computing device. Program components may be programmed using any number of different programming environments, including various languages, development kits, frameworks, and/or the like. Some or all of the functionality contemplated herein may also, or alternatively, be implemented in hardware and/or firmware.

The multilayer wearable device 202 may sense various physiological and/or environmental parameters using a sensor 212. The environmental parameters may include particulates, ultraviolet light, volatile organic compounds, and/or the like in the environment. The physiological parameters may include respiratory parameters (e.g., rate, depth, rhythm), motion parameters, (e.g., walking, running, falling, gait, gait rhythm), facial expressions, swelling, heart sounds, sweat, sweat composition (e.g., ammonia, pH, potassium, sodium, chloride), exhaled air composition, cardiac parameters, Electrocardiography (ECG) parameters, electroencephalogram (EEG) parameters, Electromyography (EMG) parameters, and/or the like. To sense the one or more environmental parameters and/or physiological parameters, the sensor 212 may include temperature sensors (e.g., thermocouples or thermistors), barometers, acoustic sensors, pressure sensors, optical sensors, motion or impact sensors (e.g., accelerometers, gyroscopes, inertial measuring units (IMUs)), strain sensors, Doppler systems, chemical sensors, ultrasound sensors, and/or the like, in any number of various types of configurations.

The I/O component 214 may include and/or be coupled to a user interface configured to present information to a user or receive indication from a user. For example, the I/O component 214 may include and/or be coupled to a display device, a speaker, a printing device, and/or the like, and/or an input component such as, for example, a microphone, a joystick, a satellite dish, a scanner, a printer, a wireless device, a keyboard, a pen, a voice input device, a touch input device, a touch-screen device, an interactive display device, a haptic device (sensor or actuator), a mouse, a volatile compound release depot, and/or the like. In embodiments, the I/O component 214 may be used to present and/or provide an indication of any of the data sensed and/or produced by the multilayer wearable device 202. According to embodiments, for example, the I/O component 214 may include one or more visual indicators (e.g., single-color LED lights, multi-color LED lights, a flexible digital display device, and/or the like) configured to provide information to a user (e.g., by illuminating, flashing, displaying data, etc.). Additionally or alternatively, the I/O component 214 may be used to control therapy provided by the multilayer wearable device 202.

The communication component 216 may be configured to communicate (i.e., send and/or receive signals) with the device 204 and/or any other device. Additionally or alternatively, any data sensed by the sensor 212 may be transmitted to the device 204 for processing and/or storage.

In embodiments, the communication component 216 may include, for example, circuits, program components, antennas, and one or more transmitters and/or receivers for communicating wirelessly with one or more other devices such as, for example, the device 204. According to various embodiments, the communication component 216 may include one or more transmitters, receivers, transceivers, transducers, and/or the like, and may be configured to facilitate any number of different types of wireless communication such as, for example, radio-frequency (RF) communication, microwave communication, infrared or visual spectrum communication, acoustic communication, inductive communication, conductive communication, and/or the like. The communication component 216 may include any combination of hardware, software, and/or firmware configured to facilitate establishing, maintaining, and using any number of communication links.

The therapy component 218 may be configured to delivery therapy in response to one or more sensed and/or derived signals. In embodiments, the therapy component 218 may include any number of different therapy components such as, for example, an inhaler component, a nebulizer component, a drug delivery component, defibrillation component, a neurostimulation component, a neuromodulation component, a temperature regulation component, and/or the like.

In embodiments, the multilayer wearable device 202 may have a transcutaneous member 220 piercing the skin of subject (e.g., subject 104). The transcutaneous member 220 may contain one or more sensors measuring parameters within a subject (i.e. a blood parameter, an interstitial fluid parameter, an electrical parameter). The transcutaneous member 220 may contain one or more components (e.g. an electrode, a catheter, a needle, a micro-needle) for delivering one or more therapies (e.g. a neurostimulation therapy, a drug therapy). In an embodiment, the transcutaneous member 220 may measure glucose and/or deliver insulin.

The power source 222 provides electrical power to the other operative components (e.g., the controller 208, the memory 210, the sensor 212, the I/O component 214, the communication component 216, and the therapy component 218), and may be any type of power source suitable for providing the desired performance and/or longevity requirements of the multilayer wearable device 202. In various embodiments, the power source 222 may include one or more batteries, which may be rechargeable (e.g., using an external energy source). The power source 222 may include one or more capacitors, energy conversion mechanisms, and/or the like. Additionally or alternatively, the power source 222 may harvest energy from a subject (e.g., the subject 104) (e.g. motion, heat, biochemical) and/or from the environment (e.g. electromagnetic). Additionally or alternatively, the power source 222 may harvest energy from an energy source connected to the body, for example, a shoe may receive energy from impact and send the received energy to a power source 222 of the multilayer wearable device 202.

As shown in FIG. 2, the device 204 includes a controller 224, a memory 226, a display device 228, a rendering component 230, an I/O component, 232 a communication component 234, and a power source 236. The controller 224 may include, for example, a processing unit, a pulse generator, and/or the like. The controller 224 may be any arrangement of electronic circuits, electronic components, processors, program components and/or the like configured to store and/or execute programming instructions, to direct the operation of the other functional components of the device 204, to store physiologic data obtained by the multilayer wearable device 202, and/or the like, and may be implemented, for example, in the form of any combination of hardware, software, and/or firmware.

In embodiments, the controller 224 may be, include, or be included in one or more Field Programmable Gate Arrays (FPGAs), one or more Programmable Logic Devices (PLDs), one or more Complex PLDs (CPLDs), one or more custom Application Specific Integrated Circuits (ASICs), one or more dedicated processors (e.g., microprocessors), one or more central processing units (CPUs), software, hardware, firmware, or any combination of these and/or other components. According to embodiments, the controller 224 may include a processing unit configured to communicate with memory to execute computer-executable instructions stored in the memory. Although the controller 224 is referred to herein in the singular, the controller 224 may be implemented in multiple instances, distributed across multiple computing devices, instantiated within multiple virtual machines, and/or the like.

The controller 224 may also be configured to store information in the memory 226 and/or access information from the memory 226. The controller 224 may execute instructions and perform desired tasks as specified by computer-executable instructions stored in the memory 226. In embodiments, for example, the controller 224 may be configured to instantiate, by executing instructions stored in the memory 226.

In embodiments, the memory 226 includes computer-readable media in the form of volatile and/or nonvolatile memory and may be removable, nonremovable, or a combination thereof. Media examples include Random Access Memory (RAM); Read Only Memory (ROM); Electronically Erasable Programmable Read Only Memory (EEPROM); flash memory; optical or holographic media; magnetic cassettes, magnetic tape, magnetic disk storage or other magnetic storage devices; data transmissions; and/or any other medium that can be used to store information and can be accessed by a computing device such as, for example, quantum state memory, and/or the like. In embodiments, the memory stores computer-executable instructions for causing the processor to implement aspects of embodiments of system components discussed herein and/or to perform aspects of embodiments of methods and procedures discussed herein.

The computer-executable instructions may include, for example, computer code, machine-useable instructions, and the like such as, for example, program components capable of being executed by one or more processors associated with the computing device. Program components may be programmed using any number of different programming environments, including various languages, development kits, frameworks, and/or the like. Some or all of the functionality contemplated herein may also, or alternatively, be implemented in hardware and/or firmware.

The display device 228 can include, but is not limited to, one of the following display devices: a cathode ray tube (CRT) display, a light emitting diode (LED) display, or a liquid crystal display (LCD) display.

The rendering component 230 may be configured to receive, from the multilayer wearable device 202, sensed physiological parameters; and cause the display device 228 to present a representation of the physiological parameters. According to embodiments, the rendering component 230 may be configured to interpret, analyze, and/or otherwise process physiological parameters prior to presenting representations thereof. In embodiments, the rendering component 230 may provide, via a GUI, interactive representations of physiological parameters. Representations of physiological parameters may include, for example, parameter values, indications of diagnoses, graphs, charts, anatomical maps, images (e.g., ultrasound images), and/or the like. According to embodiments, the rendering component 230 may also be configured to receive, via a GUI, inputs from a user that indicate parameter settings for a particular sensing task. That is, for example, the GUI may facilitate user control of any number of aspects of operation of the device 204.

The I/O component 232 in conjunction with the rendering component 230 may include and/or be coupled to a user interface configured to present information to a user or receive indication from a user. For example, the I/O component 232 may include and/or be coupled to the display device 228, a speaker, a printing device, and/or the like, and/or an input component such as, for example, a microphone, a joystick, a satellite dish, a scanner, a printer, a wireless device, a keyboard, a pen, a voice input device, a touch input device, a touch-screen device, an interactive display device, a mouse, a volatile compound release depot, and/or the like. In embodiments, the I/O component 232 may be used to present and/or provide an indication of any of the data sensed and/or produced by the multilayer wearable device 202 and/or the device 204. According to embodiments, for example, the I/O component 232 may include one or more visual indicators (e.g., single-color LED lights, multi-color LED lights, a flexible digital display device, and/or the like) configured to provide information to a user (e.g., by illuminating, flashing, displaying data, etc.).

The communication component 234 may be configured to communicate (i.e., send and/or receive signals) with the multilayer wearable device 202 and/or any other device. Additionally or alternatively, any data sensed by the sensor 212 may be transmitted to the device 204 for processing and/or storage.

In embodiments, the communication component 234 may include, for example, circuits, program components, and one or more transmitters and/or receivers for communicating wirelessly with one or more other devices such as, for example, the multilayer wearable device 202. According to various embodiments, the communication component 234 may include one or more transmitters, receivers, transceivers, transducers, and/or the like, and may be configured to facilitate any number of different types of wireless communication such as, for example, radio-frequency (RF) communication, microwave communication, infrared or visual spectrum communication, acoustic communication, inductive communication, conductive communication, and/or the like. The communication component 234 may include any combination of hardware, software, and/or firmware configured to facilitate establishing, maintaining, and using any number of communication links.

The power source 236 provides electrical power to the other operative components (e.g., the controller 224, the memory 226, the display device 228, the rendering component 230, the I/O component 232, and the communication component 234), and may be any type of power source suitable for providing the desired performance and/or longevity requirements of the device 204. In various embodiments, the power source 236 may include one or more batteries, which may be rechargeable (e.g., using an external energy source). The power source 236 may include one or more capacitors, energy conversion mechanisms, and/or the like. In embodiments, the power source 236 may transfer power to the power source 222 using a wireless or non-wireless connection (e.g., via conduction, induction, radio-frequency, etc.). Because the multilayer wearable device 202 may be a small device, as explained in more detail below, the power source 222 may not be capable of storing a lot of power and, therefore, the longevity of the multilayer wearable device 202 may be increased via power transfer from the device 204 to the multilayer wearable device 202.

The illustrative operating environment 200 shown in FIG. 2 is not intended to suggest any limitation as to the scope of use or functionality of embodiments of the present disclosure. The illustrative operating environment 200 also should not be interpreted as having any dependency or requirement related to any single component or combination of components illustrated therein. Additionally, various components depicted in FIG. 2 may be, in embodiments, integrated with various ones of the other components depicted therein (and/or components not illustrated), all of which are within the ambit of the present disclosure.

Figure 3:
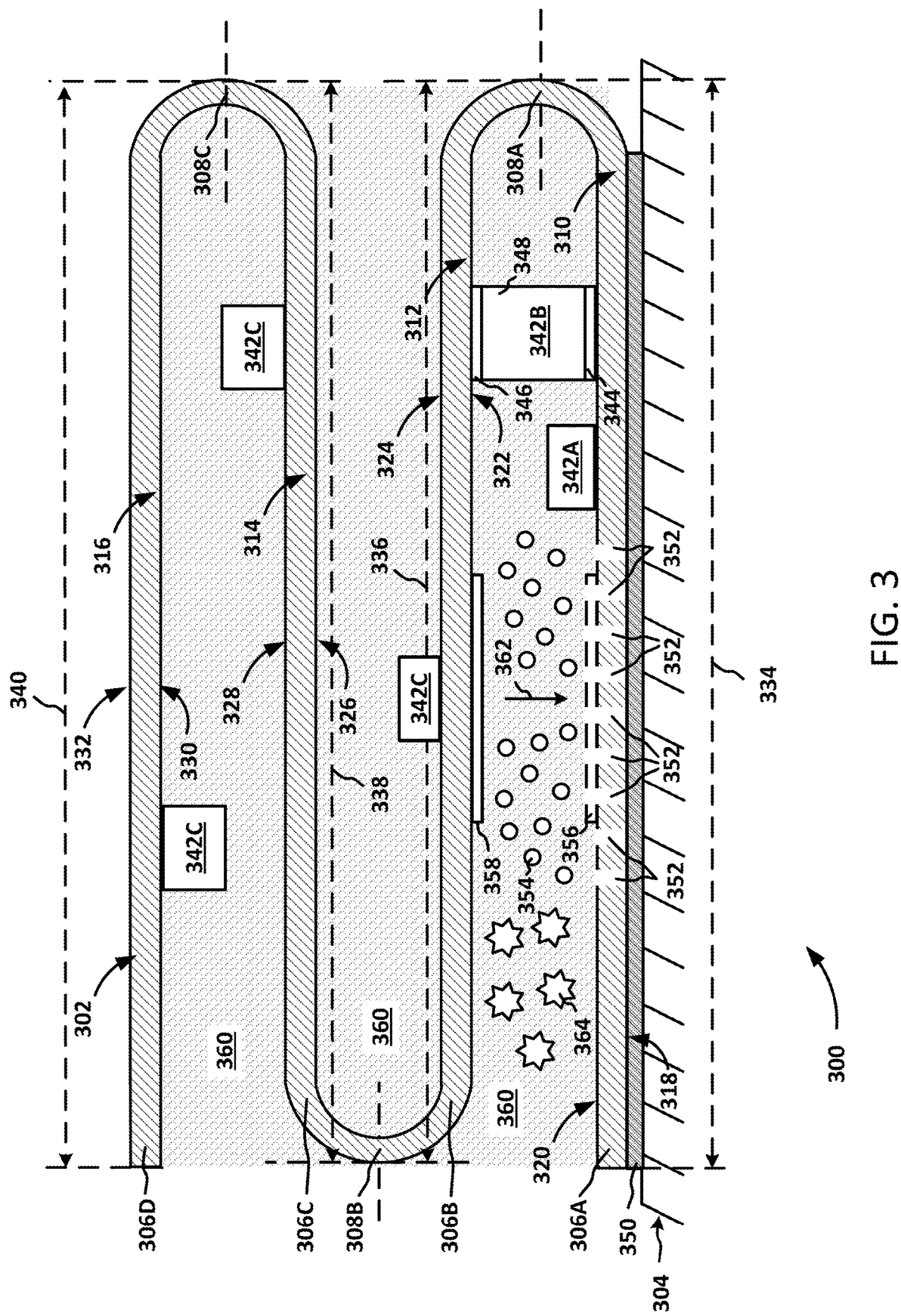
FIG. 3 is a schematic illustration of a side sectional view of a multilayer wearable device, in accordance with embodiments of the disclosure.

FIG. 3 is a schematic illustration of a side sectional view of a multilayer wearable device 300, in accordance with embodiments of the disclosure. The multilayer wearable device 300 may be formed from a substrate 302 and be configured to be attached to a subject 304. The substrate 302 may be a continuous substrate that facilitates printing a number of electronic components thereon, as explained below.

As illustrated, the multilayer wearable device 300 includes multiple layers 306A-306D. To form the layers 306A-306D, the substrate 302 may be folded, bent, and/or arranged. For example, the substrate 302 may be folded, bent and/or arranged at a first junction 308A, a second junction 308B, and/or a third junction 308C to form four layers 306A-306D. The first junction 308A may separate a first portion 310 of the substrate 302 from a second portion 312 of the substrate 302. The second junction 308B may separate the second portion 312 from a third portion 314. And the third junction 308C may separate the third portion 314 from a fourth portion 316.

As illustrated, each portion 310-316 has two sides, a first side and a second that is opposite the first side. For example, the first portion 310 has a first side 318 configured to be attached to a subject 304 and a second side 320 opposite the first side 318. The second portion 312 has a first side 322 and a second side 324 opposite the first side 322. The third portion 314 has a first side 326 and a second side 328 opposite the first side 326. And, the fourth portion 316 has a first side 330 and a second side 332 opposite the first side 330. In embodiments when the substrate 302 is folded, bent and/or arranged at the first junction 308A, the second side 320 of the first portion 310 opposes and is disposed adjacent to the first side 322 of the second portion 312. Further, in embodiments when the substrate 302 is folded, bent and/or arranged at the second junction 308B, the second side 324 of the second portion 312 opposes and is disposed adjacent to the first side 326 of the third portion 314. And, in embodiments when the substrate 302 is folded, bent and/or arranged at the third junction 308C, the second side 328 of the third portion 314 opposes and is adjacent to the first side 330 of the fourth portion 316 and the second side 332 of the fourth portion 316 forms an outer surface of the multilayer wearable device 300. While the term "adjacent" is used to describe the orientation of the first sides 318, 322, 326, 330 with respect to the second sides 320, 324, 328, 332 of the portions 310-316, a gel or other components may be arranged between the first sides 318, 322, 326, 330 and the second sides 320, 324, 328, 332 as described below.

While four layers 306A-306D and three junctions 308A-308C are depicted, the multilayer wearable device 300 may only include two layers 306A-306B and one junction 308A.

Alternatively, the multilayer wearable device 300 may include more than four layers 306A-306D and more than three junctions 308A-308C. Other types of configurations are also contemplated herein. For example, the first layer 306A may be a first hemicylinder of a first portion of tubular element and the second layer 306B may be the second hemicylinder of the first portion that opposes the first hemicylinder of the first portion (i.e., the first layer 306A). Additionally or alternatively, the third layer 306C may be a first hemicylinder of a second portion of the tubular element and the fourth layer 306D may be a second hemicylinder of the second portion that opposes the first hemicylinder of the second portion (i.e., the third layer 306C). In embodiments, the first portion of the tubular element may be separated from the second portion of the tubular element by a radial dissection. The radial dissection may occur at the midpoint of the tubular element or other locations of the tubular element away from the midpoint. In embodiments, the second portion may be folded onto the first portion at a first junction to form the wearable device. This exemplary wearable device may include any of the features included in the wearable device 300.

Referring to FIG. 3, the substrate 302 may be folded, bent and/or arranged in a manner that the width 334 of an outer envelope of the first portion 310 may be greater than or equal to a width 336 of an outer envelope of the second portion 312, a width 338 of an outer envelope of the third portion 314, and/or a width 340 of an outer envelope of the fourth portion 316. Alternatively, the width 334 of an outer envelope of the first portion 310 may be less than or equal to a width 336 of an outer envelope of the second portion 312, a width 338 of an outer envelope of the third portion 314, and/or a width 340 of an outer envelope of the fourth portion 316. The outer envelope for each respective portion 310-316 delimits an outer most bound of the respective portion 310-316. For example, an outer envelope of the first portion 310 includes the first portion 310 but doesn't include additional space beyond the exterior of the first portion 310.

As illustrated, one or more electronic components 342A-342C may be arranged on one or more of the portions 310-316. An exemplary electronic component 342A may be one or more sensors (e.g., sensor 212) configured to sense one or more physiological parameters and/or environmental parameters using electrical, mechanical, optical, and/or chemical means. The physiological parameters may include respiratory parameters (e.g., rate, depth, rhythm), motion parameters, (e.g., walking, running, falling, gait, gait rhythm), facial expressions, swelling, heart sounds, sweat, sweat composition (e.g., ammonia, pH, potassium, sodium, chloride), exhaled air composition, Electrocardiography (ECG) parameters, electroencephalogram (EEG) parameters, Electromyography (EMG) parameters, and/or the like. In embodiments, the electronic components 342A-342C may include processing devices configured to process the sensed parameters, memory to store the sensed parameters, transmitters to transmit the sensed parameters, and/or receivers to receive one or more transmissions. The environmental parameters may include particulates, ultraviolet light, volatile organic compounds, and/or the like in the environment.

In embodiments the materials comprising the first junction 308A, the second junction 308B, and/or the third junction 308C of substrate 302 may be the same as the materials used elsewhere in substrate 302. In other embodiments the materials comprising the first junction 308A, the second junction 308B, and/or the third junction 308C of substrate 302 may be different than the materials used elsewhere in substrate 302. In at least some embodiments, the materials in junctions 308A, 308B and/or 308C may be more flexible, have shape-memory alloy properties, have greater abrasion resistance and/or have greater mechanical flex fatigue resistance than the materials used elsewhere in substrate 302. Additionally or alternatively, junctions 308A, 308B and/or 308C may be comprised of fewer or additional materials as compared to elsewhere in substrate 302.

Another exemplary electronic component 342B may be a capacitor. The capacitor 342B may be arranged between the first portion 310 and the second portion 312, between the second portion 312 and the third portion 314, and/or between the third portion 314 and the fourth portion 316. For example, the capacitor 342B may include a first conductive surface 344 arranged on a second side 320 of the first portion 310 and a second conductive surface 346 arranged on a first side 322 of the second portion 312 such that the first conductive surface 344 is electrically isolated from the second conductive surface 346. In embodiments, respective electrical leads may be attached to the conductive surfaces 344, 346. In embodiments, a deformable dielectric 348 may be arranged between the first conductive surface 344 and the second conductive surface 346. In embodiments, electrical signals sensed by the electrical leads connected to the conductive surfaces 344, 346 may be used to determine a change in capacitance of the capacitor 342B and based on the elastic modulus of the dielectric 348, a pressure on the multilayer wearable device 300 may be determined.

Other exemplary electronic components 342C include, but are not limited to controllers (e.g., controller 208), memory (e.g., memory 210), I/O components (e.g., I/O components 214), communication components (e.g., communication components 216), therapy components (e.g., therapy components 218), transcutaneous members (e.g., transcutaneous members 220), and/or power sources (e.g., power sources 222).

As stated above, the multilayer wearable device 300 may be arranged on a subject 304 (e.g., the skin of the subject 304). For example, the first side 318 of the first portion 310 may be configured to contact and adhere to the subject 304. In embodiments, the first side 318 of the first portion 310 may include an adhesive 350 that adheres to the subject 304. Additionally or alternatively, the adhesive 350 may be applied to the first side 318 of the first portion 310 and/or the subject 304 in order to adhere the multilayer wearable device 300 to the subject 304. Exemplary adhesives 350 include but are not limited to silicon-based adhesives, e.g. Silpuran® 2130 and/or Silbione 4717, and/or acrylic-based adhesives. Additionally or alternatively, one or more antibiotic materials may be incorporated into the adhesive 316 to, for example, extend the use of the wearable device 300. For example, one or more antibiotic materials may be incorporated into the adhesives 316: metal salts and/or metal ions (e.g. copper, silver), antibiotics (e.g., neomycin, soframycin, bacitracin, polymycin), antibacterials, (e.g., chlorhexidine), its salts (e.g., quaternary ammonium compounds—cetrimide, domiphen bromide, polymeric quaternaries) and/or iodophors (e.g., povidone iodine).

As stated above, because the multilayer wearable device 300 includes multiple layers, more electronic components may be arranged on the multilayer wearable device 300 while maintaining a smaller contact interface between the multilayer wearable device and a subject 304 (e.g., the contact interface between the first portion 310 and the subject 304) than if the multilayer wearable device 300 were a single layer. For example, in the event the device were a single layer device and the device included the same size substrate 302, the interface between the device and the subject 304 would be approximately four times as large, assuming each of the portions 310-316 are approximately the same size. As such, the multilayer wearable device 300 may have a smaller footprint than another single-layer wearable device while providing the same or more functionality than the single-layer wearable device. Having a smaller footprint while having the same or more functionality may be beneficial in the event the multilayer wearable device 300 is arranged on a subject in an area with limited available space (e.g., on an eyelid, on an earlobe, underneath a tongue, etc.).

In embodiments, one or more portions 310-316 of the substrate 302 may be flexible and/or stretchable. Exemplary materials the substrate 302 may be comprised of include, but are not limited to: metal film, silicon, graphene, polyester (PET), polyimide (PI), polyethylene naphthalate (PEN), polyetherimide (PEI), fluropolymers (FEP), copolymers, and/or the like.

In embodiments, the portions 310-316 may only be flexible (e.g., bendable) and not stretchable (e.g., capable of being elongated without breaking). In other embodiments, the portions 310-316 may be both flexible and stretchable. In embodiments, different portions 310-316 of the substrate 302 may have different flexibility and/or stretchiness. For example, because the first portion 310 is arranged in contact with the subject 304, the first portion 310 may be more flexible and/or stretchable than the other portions 312-316. As stated above, the flexible and/or stretchable characteristics of the multilayer wearable device 300 may allow the multilayer wearable device 300 to be placed in positions on a subject 304 where another, more rigid device may not be able to be placed and/or where a more rigid device may be uncomfortable for the subject. As such, the multilayer wearable device 300 may be able to sense parameters that a more rigid device may not be able to sense.

In embodiments, the second portion 312, the third portion 314, and/or the fourth portion 316 may be thicker than the first portion 310 to facilitate protecting the first portion 310 and/or electronic components 342 on the first portion 310 and/or between the first portion 310 and the second portion 312. For example, the thickness of the first portion 310 may be equal to or less than 10 micrometers and the thickness of the second portion 312, the third portion 314, and/or the fourth portion 316 may be greater than 10 micrometers.

As another example, the second portion 312, the third portion 314, and/or the fourth portion 316 may be the same thickness as the first portion 310, but the second portion 312, the third portion 314, and/or the fourth portion 316 may be more rigid than the first portion 310 due to: (i) a coating applied to the second portion 312, the third portion 314, and/or the fourth portion 316, (ii) the second portion 312, the third portion 314, and/or the fourth portion 316 being constructed of different materials than the first portion 310, and/or (iii) the second portion 312, the third portion 314, and/or the fourth portion 316 being thicker than the first portion 310.

In embodiments, the first portion 310 may be porous and include one or more pores 352 that penetrate the entire thickness of the first portion 310. In embodiments, the pores 352 may be of a size that allows an active pharmaceutical ingredient 354 to pass through the first portion 310 to the subject 304. As such, the multilayer wearable device 300 may be used to deliver an active pharmaceutical ingredient 354 to the subject 304 by disposing the active pharmaceutical ingredient 354 between one or more of the layers 306A-306D of the multilayer wearable device 300.

Examples of active pharmaceutical ingredients 354 include, but are not limited to: anti-bacterial components, anti-asthmatic compounds (e.g., Zileuton), pharmaceutical ingredients used in epicutaneous immunotherapy, nitroglycerin, testosterone, nicotine, opiate (e.g. Fentanyl, Buprenorphine), antimuscarinic (e.g. Scopolamine, Oxybutynin), estrogen (e.g. Estradiol, Estradiol, Norethisterone Acetate), contraceptive (e.g. Norelgestromin & EthinylEstradiol), monoamine oxidase (MAO) inhibitors (e.g. Selegeline), dopamine agonists (e.g. Rotigotine), cholinesterase inhibitors (e.g. Rivastigmine), 5HT3 inhibitors (e.g. Granisetron), central nervous system stimulants (e.g. Methylphenidate), alpha-agonist hypotensive (e.g. Clonidine). Additionally or alternatively, the active pharmaceutical ingredient 354 may be triggered to release during specific part/time of the day (e.g., only during sleep), during a trigger event (e.g., a specific heart rate, during exercise and/or the like.

To facilitate delivery of the active pharmaceutical ingredient 354, a first electrode 356 may be arranged (e.g., printed) on the second side 320 of the first portion 310 and a second electrode 358 may be arranged on the first side 322 of the second portion 312. In embodiments, the pores 352 may extend through the first electrode 356. In order to facilitate delivery of the active pharmaceutical ingredient 354, the electrodes 356, 358 may be connected to electrical leads (not shown) in order to produce a potential difference therebetween. When a voltage is applied to the electrodes 356, 358, and either the active pharmaceutical ingredient 354 has a charge or a substance 360 disposed between the first portion 310 and the second portion 312 has a charge, the active pharmaceutical ingredient 354 may be biased in the direction 362 towards the first portion 310 through the pores 352 and in contact with the subject 304. As such, the multilayer wearable device 300 may facilitate delivering an active pharmaceutical ingredient 354 to the subject 304.

In embodiments, a substance 360 may be arranged between the layers 306A-306D of the multilayer wearable device 300. In embodiments, the substance 360 may facilitate separation of the portions 310-316 from each other. For example, the substance 360 may be disposed between the first portion 310 and the second portion 312 to facilitate separation between the portions 310, 312. As another example, the substance 360 may be disposed between the second portion 312 and the third portion 314 to facilitate separation between the portions 312, 314. As even another example, the substance 360 may be disposed between the third portion 314 and the fourth portion 316 to facilitate separation between the portions 314, 316.

In embodiments, the substance 360 may be a gel 360. Exemplary gels 360 include but are not limited to: AMPS (2-acrylamido-2-methylpropane sulfonic acid sodium salt), PEGDA (polyethylene glycol diacrylate), PVA (Polyvinyl alcohol), PVP (Polyvinyl pyrrolidone), PEG (polyethylene glycol), Chitosan, keratin, and/or the like. Additionally, the gel 436 may include one or more particles (e.g., microparticles) (not shown). Additionally, the gel 360 may include one or more particles 364 (e.g., micro-particles). In embodiments, the particles may assist the gel 360 in maintaining separation between the portions 310-316 and/or make the gel 360 more viscous to reduce the likelihood the gel 360 emanates from the multilayer wearable device 300. Exemplary particles 364 include but are not limited to Poly (methyl methacrylate) (PMMA), silica, polystyrene, glass, round particles ranging from 0.1 micrometers to 50 micrometers, and/or the like.

Figure 4:
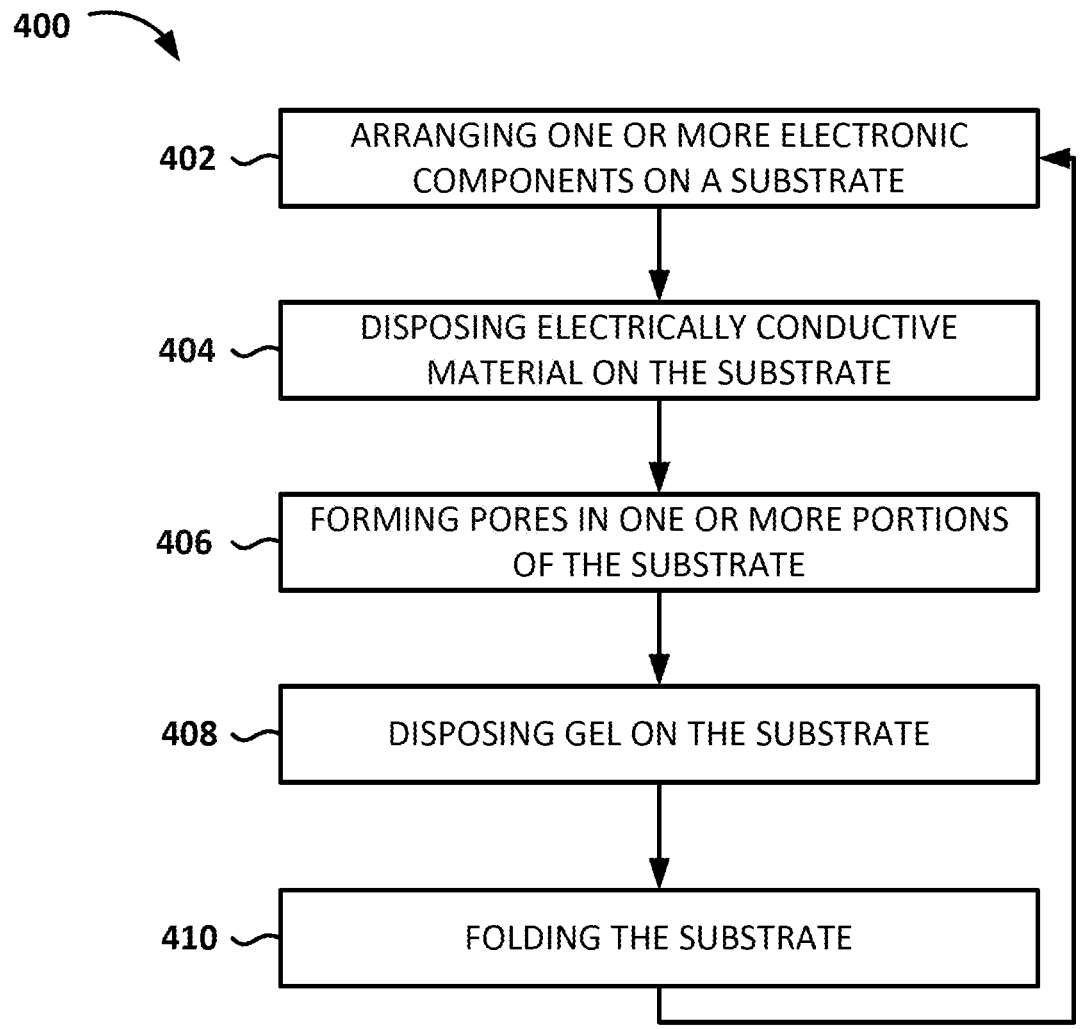
FIG. 4 is a flow diagram illustrating a method of manufacturing a multilayer wearable device configured to be attached to a subject, in accordance with embodiments of the disclosure.

FIG. 4 is a flow diagram illustrating a method 400 of manufacturing a multilayer wearable device configured to be attached to a subject, in accordance with embodiments of the disclosure. In embodiments, the method 400 comprises arranging one or more electronic components on a substrate (block 402). In embodiments, the substrate may be the same or similar to the substrate 302 described above. Additionally or alternatively, the one or more electronic components may be the same or similar to the electronic components 342 described above. For example, one or more of the electronic components may be configured to sense physiological and/or environmental parameters. The physiological parameters may include respiratory parameters (e.g., rate, depth, rhythm), motion parameters, (e.g., walking, running, falling, gait, gait rhythm), facial expressions, swelling, heart sounds, sweat, sweat composition (e.g., ammonia, pH, potassium, sodium, chloride), exhaled air composition, Electrocardiography (ECG) parameters, electroencephalogram (EEG) parameters, Electromyography (EMG) parameters, and/or the like. The environmental parameters may include particulates, ultraviolet light, volatile organic compounds, and/or the like in the environment.

In embodiments, the method 400 may further comprise disposing (e.g., printing) electrically conductive material on the substrate (block 404). The electrically conductive material may be the same or similar to the electrodes 356, 358 and/or the conductive surfaces 344, 346 described above. For example, a first electrode and/or a first conductive surface may be arranged on a second side of a first portion of the substrate and a second electrode and/or a second conductive surface may be arranged on a first side of a second portion of the substrate. In embodiments, the electrically conductive material may facilitate delivering an active pharmaceutical ingredient to a subject and/or used in a capacitor to measure pressure on the multilayer wearable device.

In embodiments, the method 400 may further comprise forming pores in one or more portions of the substrate (block 406). In embodiments, the pores may be the same or similar to the pores 352 discussed above. For example, the pores may completely penetrate a first portion of the substrate in order to allow an active pharmaceutical ingredient to penetrate the substrate and be delivered to a subject. In embodiments, the pores 352 may also penetrate an electrically conductive surface arranged on the substrate.

The method 400 may further comprise disposing a gel on the substrate (block 408). The gel may be the same or similar as the gel 360 described above. For example, the gel may facilitate separation between the portions of the substrate once folded, bent and/or arranged and/or include particles to aid in the separation and reduce the likelihood the gel emanates from the multilayer wearable device.

In embodiments, the method 400 may further comprise folding, bending, and/or arranged the substrate (block 410). The substrate may be folded, bent and/or arranged in a manner so that the multilayer wearable device has the same or similar characteristics as the multilayer wearable device 300. For example, the substrate may be folded, bent and/or arranged at a first junction. The first junction may separate a first portion and a second portion, where the first portion is connected to the second portion. The first side of the first portion may be configured to attach to a subject and the second side of the first portion is arranged adjacent to the first side of the second portion.

In embodiments, one or more portions of the method 400 may be repeated. For example, one or more electronic components may be arranged on a second side of the second portion, a gel may be arranged on the second side of the second portion, and/or the substrate may be folded, bent and/or arranged at a second junction so the second side of the second portion may be arranged adjacent to a first side of a third portion of the substrate. In embodiments, one or more electronic components may be arranged on a second side of the third portion, a gel may be arranged on the second side of the third portion, and/or the substrate may be folded, bent and/or arranged at a third junction so the second side of the third portion is arranged adjacent to a first side of a fourth portion of the substrate.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

What is claimed is:

1. A multilayer wearable device configured to be attached to a subject, the multilayer wearable device comprising:
   a single continuous substrate folded to form multiple layers, the substrate comprising a first portion and a second portion, the first portion having a first side and a second, opposite side, and the second portion having a first side and a second, opposite side;
   wherein the first side of the first portion is configured to be attached to the subject and the second portion is arranged on top of the first portion such that the first side of the second portion faces the second side of the first portion;
   a first electrical component arranged on the first portion of the substrate and configured to sense a physiological parameter of the subject;
   a second electrical component arranged on the second portion of the substrate; and
   a gel layer arranged between the first portion and the second portion,
   wherein the first portion is porous to an active pharmaceutical ingredient such that the active pharmaceutical ingredient is able to transmit through the first portion to the subject.

2. The multilayer wearable device of claim 1, wherein the second portion has a greater thickness than the first portion.

3. The multilayer wearable device of claim 1, wherein the first portion is flexible and stretchable.

4. The multilayer wearable device of claim 1, further comprising a first electrode arranged on the second side of the first portion and a second electrode arranged on the first side of the second portion, wherein the first electrode is not electrically connected to the second electrode, wherein the first electrode and the second electrode are configured to facilitate delivery of the active pharmaceutical ingredient to the subject via application of a voltage to the first electrode or the second electrode.

5. The multilayer wearable device of claim 1, the gel layer further comprising particles configured to facilitate separation between the first portion and the second portion.

6. The multilayer wearable device of claim 1, wherein the first electrical component comprises a capacitor arranged between the first portion and the second portion, wherein the capacitor facilitates measuring a pressure applied to the multilayer wearable device.

7. The multilayer wearable device of claim 1, wherein the thickness of the substrate is less than or equal to approximately 10 micrometers.

8. The multilayer wearable device of claim 1, the substrate comprising a third portion having a first side and a second, opposite side, wherein the third portion is arranged on top of the second portion such that the first side of the third portion is disposed adjacent the second side of the second portion.

9. The multilayer wearable device of claim 1, wherein a width of an outer envelope of the first portion is greater than or equal to a width of an outer envelope of the second portion.

10. A method of manufacturing a multilayer wearable device configured to be attached to a subject, the method comprising:
arranging an electrical component on a single continuous substrate, wherein the electrical component is configured to sense a physiological parameter of the subject; and
folding the substrate to form the multilayer wearable device, wherein a first junction of the substrate separates a first portion and a second portion of the substrate, the first portion having a first side and a second, opposite side, and the second portion having a first side, and a second, opposite side; and
forming pores in the first portion, wherein the pores are porous to an active pharmaceutical ingredient such that the active pharmaceutical ingredient is able to transmit through the first portion to the subject,
wherein the first side of the first portion is configured to be attached to the subject, and the second portion is arranged on top of the first portion such that the first side of the second portion faces the second side of the first portion.

11. The method of claim 10, further comprising disposing a gel on the second side of the first portion.

12. The method of claim 11, the gel layer further comprising particles configured to facilitate separation between the first portion and the second portion.

13. The method of claim 10, the method further comprising disposing a first electrode on the second side of the first portion and a second electrode on the first side of the second portion, wherein the first electrode is not electrically connected to the second electrode, wherein the first electrode and the second electrode facilitate delivery of an active pharmaceutical ingredient to the subject via application of a voltage to the first electrode or the second electrode.

14. The method of claim 10, further comprising arranging the substrate so that a second junction separates the second portion and a third portion, the third portion having a first side and a second, opposite side, wherein the third portion is arranged on top of the second portion such that the first side of the third portion is disposed adjacent the second side of the second portion.

15. The method of claim 14, further comprising disposing a gel on the second side of the second portion.

16. The method of claim 10, wherein the second portion has a greater thickness than the first portion.

* * * * *